(12) United States Patent
Merkle et al.

(10) Patent No.: US 6,515,139 B1
(45) Date of Patent: Feb. 4, 2003

(54) METHOD FOR PRODUCING N-SUBSTITUTED 2-PYRAZOLINE-5-ONE

(75) Inventors: Hans Rupert Merkle, Ludwigshafen (DE); Erich Fretschner, Neckarsteinach (DE); Knut Koob, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 191 days.

(21) Appl. No.: 10/129,990
(22) PCT Filed: Nov. 17, 2000
(86) PCT No.: PCT/EP00/11439

§ 371 (c)(1),
(2), (4) Date: May 13, 2002

(87) PCT Pub. No.: WO01/36389

PCT Pub. Date: May 25, 2001

(30) Foreign Application Priority Data

Nov. 19, 1999 (DE) .......................................... 199 55 800

(51) Int. Cl.⁷ .............................................. C07D 231/20
(52) U.S. Cl. ................................................... 548/366.1
(58) Field of Search ....................................... 548/366.1

(56) References Cited

U.S. PATENT DOCUMENTS

| 4,557,753 A | 12/1985 | Tanaka et al. |
| 4,931,565 A | 6/1990 | Baba et al. |

OTHER PUBLICATIONS

Dorn et al. "Alkylierung 1–acylierter Pyrazolidone–(3) und Synthesen 2–Substituierter Pyrazolidone–(3) sowie 1–substituierter 5–Hydroxy–pyrazole" Jnl. Praktische Chemie vol. 313 (1971) pp. 115–128.

*Primary Examiner*—Robert W. Ramsuer
(74) *Attorney, Agent, or Firm*—Keil & Weinkauf

(57) ABSTRACT

The present invention relates to a process for preparing N-substituted 2-pyrazolin-5-ones of the formula I

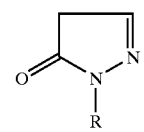

(I)

where R has the meaning given in claim 1, which comprises reacting a compound of the formula II

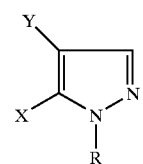

(II)

where R, X and Y have the meanings given in claim 1, at elevated temperature with a molar excess of alkali metal hydroxide in an aqueous reaction medium and then adjusting the pH to pH≦6 by adding an acid.

6 Claims, No Drawings

METHOD FOR PRODUCING N-SUBSTITUTED 2-PYRAZOLINE-5-ONE

The present invention relates to a process for preparing N-substituted 2-pyrazolin-5-ones of the formula I

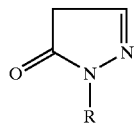

(I)

in which

R is $C_1$–$C_8$-alkyl, $C_5$–$C_8$-cycloalkyl, phenyl, naphthyl or phenyl-$C_1$–$C_4$-alkyl which may be unsubstituted or may carry one or more substituents which are inert towards aqueous alkali.

N-Substituted pyrazolinones are useful intermediates for preparing pharmaceuticals and crop protection agents. Thus, for example, U.S. Pat. No. 4,557,753 describes the preparation of benzoyl-substituted 5-benzyloxy-1-methylpyrazoles which are prepared starting from 1-methylpyrazolin-5-one.

In general, N-substituted pyrazolones are prepared by cyclization of β-functionalized acid derivatives with substituted hydrazines. A review of various synthesis methods is given in EP-A 240 001. This publication furthermore describes a process in which a hydrazone of a β-hydrazinopropionic acid derivative is cyclized in the presence of a base. In all of the processes mentioned, substituted hydrazines are employed. Firstly, substituted hydrazines are difficult to obtain and thus expensive. Secondly, substituted hydrazines are usually highly toxic. Accordingly, it is desirable to prepare N-substituted pyrazolinones from already known or otherwise obtainable pyrazole precursors.

Dorn et al. (J. Pract. Chem. 313 (1971), 115–128) describe a process in which 3-pyrazolidone is initially acylated at the 1-nitrogen, then alkylated with alkyl chlorides or dialkyl sulfates at the 2-nitrogen, followed by removal of the acyl group under oxidizing conditions. This gives N-substituted 5-hydroxypyrazoles or their tautomers, i.e. 2-pyrazolin-5-ones. However, owing to the large number of reaction steps, the preparation process is uneconomical. Moreover, dialkyl sulfates are highly toxic.

It is an object of the present invention to provide an economical process for preparing the 2-pyrazolin-5-ones of the formula I defined at the outset, which process uses pyrazoles which are already known or easily obtainable as starting materials.

We have found that this object is achieved and that compounds of the formula I are obtained in good yields by reacting 5-halopyrazole-4-carboxylic acids or derivatives thereof which can be hydrolyzed with bases at elevated temperature with aqueous alkali metal hydroxide solutions and then acidifying the reaction mixture.

Accordingly, the present invention relates to a process for preparing N-substituted 2-pyrazolin-5-ones of the formula I defined at the outset, which process comprises reacting a compound of the formula II

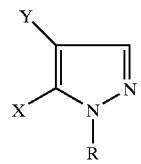

(II)

in which

X is halogen, and

Y is CN or a group of the formula R'(O)C, in which R' is a hydroxyl group or a radical which can be hydrolyzed using alkali metal hydroxide, and R has the meanings mentioned for formula I, at elevated temperature with a molar excess of alkali metal hydroxide in an aqueous reaction medium, and then adjusting the pH to pH≦6 by adding an acid.

Hereinbelow, compounds of the formula II where Y=R'(O)C and R'=OH are also referred to as 5-halopyrazole-4-carboxylic acids, and the compounds where Y=CN or Y=R'(O)C where R'≠OH are referred to as 5-halopyrazole-4-carboxylic acid derivatives.

The compounds of the formula I are in an equilibrium with the 5-hydroxypyrazoles of the formula Ia

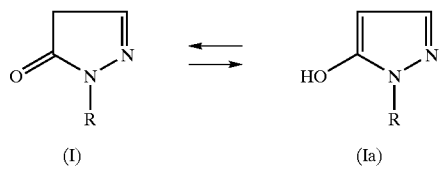

(I)                              (Ia)

Accordingly, the process according to the invention also embraces the preparation of the compounds Ia.

Organic radicals R' which can be hydrolyzed under basic reaction conditions, such as alkali metal hydroxide, are known to the person skilled in the art. Examples of suitable radicals R' are $C_1$–$C_4$-alkoxy, such as methoxy, ethoxy, n-propoxy and n-butoxy, which may also be substituted, and furthermore phenyloxy and benzyloxy, which may also be substituted at the phenyl ring. Examples of substituents are halogen, such as fluorine, chlorine or bromine, furthermore nitro and $C_1$–$C_4$-alkoxy. Further radicals R' which can be hydrolyzed with base are $NH_2$ and halogen. Preferred radicals R' which can be hydrolyzed with base are $C_1$–$C_4$-alkoxy, in particular methoxy and ethoxy. If Y is a group CN, i.e. the compound II is a nitrile derivative, under the reaction conditions of the first step the nitrile group is hydrolyzed to the carboxyl group. This also applies when Y is R'(O)C and R' is a group which can be hydrolyzed with alkali metal hydroxide.

Particularly preferred compounds II are the carboxylic acids, i.e. the radical R' is hydroxyl (=OH). Also preferred are compounds II in which Y is R'(O)C and R' is $C_1$–$C_4$-alkoxy, in particular methoxy or ethoxy.

According to the invention, preferred halogen X is chlorine or bromine, in particular chlorine.

For the reaction according to the invention, the nature of the substituent R is of minor importance. The meanings mentioned for R are collective terms for individual radicals. These meanings are:

$C_1$–$C_8$-alkyl: a linear or branched alkyl chain having 1 to 8 carbons, for example methyl, ethyl, n-propyl, isopropyl, n-butyl, 2-butyl, isobutyl, tert-butyl, n-pentyl, 2-methylbutyl, 2,2-dimethylpropyl, n-hexyl, 1-methylpentyl, 2-methylpentyl, 1-ethylbutyl, 2-ethylbutyl, n-heptyl, n-octyl and 2-ethylhexyl.

$C_3$–$C_8$-cycloalkyl: mono- or bicyclic hydrocarbon radicals having 3 to 8 carbon atoms, for example cyclopropyl, cyclobutyl, cyclopentyl, cyclohexyl, cycloheptyl, cyclooctyl, norbornyl and 2.2.2-bicyclooctyl.

Phenyl-$C_1$–$C_4$-alkyl is a $C_1$–$C_4$-alkyl group which is substituted by phenyl, for example benzyl, 1-phenylethyl and 2-phenylethyl.

The abovementioned radicals, and phenyl and naphthyl, may have one or more substituents which are inert towards aqueous alkali metal hydroxide solutions. Examples of such radicals are $C_1$–$C_4$-alkoxy, such as methoxy, ethoxy, propoxy, n-butoxy, tert-butoxy, furthermore trifluoromethyl, pentafluoroethyl, trifluoromethoxy and pentafluoroethoxy. Another suitable alkali-stable substituent for the radicals cycloalkyl, phenyl, naphthyl and phenyl-$C_1$–$C_4$-alkyl is $C_1$–$C_4$-alkyl. The three last-mentioned substituents may also have one or more chlorine or fluorine atoms as alkali-inert substituents at the phenyl group or the naphthyl group.

R is preferably $C_1$–$C_8$-alkyl and in particular $C_1$–$C_4$-alkyl, which are preferably unsubstituted, and is particularly preferably methyl or ethyl.

The starting materials of the formula II are known to the person skilled in the art and readily obtainable (see EP-A 350176). Compounds of the formula II which are not known can be prepared for example in a simple manner by oxidation of N-substituted 5-halo-4-methylpyrazoles by the process described in EP-A 350 176.

In the process according to the invention, in a first step, a compound of the formula II is reacted with alkali metal hydroxide in molar excess in an aqueous reaction medium. In the case of the compounds of the formula II, a molar excess of alkali metal hydroxide is ensured when more than 2 mol of alkali metal hydroxide are employed per mole of the compound II. In the first step, one mole is required for exchanging the halogen X with hydroxyl and one mole is required for hydrolysis or neutralization of the group C(O)R'. According to the invention, preference is given to using 3 to 20 mol of alkali metal hydroxide and in particular 5 to 12 mol of alkali metal hydroxide per mole of the compound II. Preferred alkali metal hydroxides are sodium hydroxide and potassium hydroxide, in particular sodium hydroxide.

Suitable aqueous reaction media are both water and mixtures of water and water-miscible organic solvents. The water-miscible organic solvents are preferably inert to alkali metal hydroxide under the reaction conditions. Examples of suitable organic solvents are $C_1$–$C_4$-alkanols, in particular methanol and ethanol, and furthermore dimethyl sulfoxide, tetrahydrofuran, dioxane, glycol, glycerol, diethylene glycol, triethylene glycol and the like. In general, the aqueous reaction medium does not contain more than 50% by volume, preferably not more than 30% by volume and in particular not more than 10% by volume of an organic ater-miscible solvent. In a preferred embodiment of the present invention, water is the only solvent.

The first reaction step is particularly preferably carried out in an aqueous alkali metal hydroxide solution which contains 10 to 50% by weight and in particular 20 to 40% by weight of alkali metal hydroxide.

According to the invention, the first reaction step is carried out at elevated temperature. Elevated temperature is understood as meaning heating at, in general, at least 50° C. and, preferably, at least 90° C. In general, a reaction temperature of 200° C. is not exceeded. Very particularly preferably, the reaction is carried out at temperatures in the range from 120 to 200° C.

Depending on the reaction temperature, the first reaction step is carried out under atmospheric pressure or under elevated pressure. At reaction temperatures above 100° C., a reaction pressure of from 1 to 10 bar is usually obtained. Typical reaction conditions are, for example in the case of a purely aqueous reaction medium, 150–1800C and 5–7 bar.

In general, the reaction is carried out until the starting material II has been converted virtually completely. Conversion is understood here as meaning the conversion of the halogen group X in the pyrazole II into a hydroxyl group or the formation of the corresponding alkoxide and the hydrolysis of the nitrile group (X=CN) or the group —C(O)R', if R'≠OH. The time required for achieving virtually complete conversion naturally depends on the chosen reaction conditions and can vary between 0.5 h and 24 h. Typical reaction times in purely aqueous systems are generally in the range from 2 to 10 h.

In the second reaction step, the reaction product obtained in the first reaction step is reacted under acidic conditions. with evolution of $CO_2$, the compound I is formed. The evolution of $CO_2$ is due to the elimination of the carboxyl group in the 4-position of the pyrazole ring which is, if appropriate, formed by hydrolysis of the group C(O)R'.

The second reaction step is generally carried out without isolating the reaction product formed in the first reaction step. The second reaction step is preferably initiated by adding an acid to the reaction mixture of the first reaction mixture. If appropriate, it is also possible to remove some or all of the aqueous solvent of the first reaction step before carrying out the second reaction step and replacing it with a new solvent, preferably an aqueous solvent and in particular with water. This procedure is suitable in particular when in the first step an organic solvent has been used which, for example owing to a volatility which is comparable to that of the compound I, or otherwise, makes the isolation of the compound I more difficult.

According to the invention, the second reaction step is carried out under acidic conditions, i.e. the pH of the reaction mixture in the second reaction step is 6 or less and preferably in the range from 1 to 3. The pH is preferably not less than 0. The pH is adjusted by adding an acid to the reaction product of the first reaction step. Preferably, the acid is added to the aqueous reaction mixture of the first reaction step. In general, the reaction mixture of the first reaction step will be cooled to a temperature suitable for the second reaction step, which is generally in the range from 0 to 100° C. and preferably in the range from 10 to 50° C., and the acid is then added.

Suitable acids are, in principle, all acids which have an acid strength which is sufficient for achieving the desired pH. If the second reaction step is carried out directly after the first reaction step, it has to be taken into consideration that excess alkali metal hydroxide has still to be neutralized. For this reason, a strong acid, preferably a mineral acid, such as hydrochloric acid, sulfuric acid or phosphoric acid, will be used for adjusting the pH. The acids and in particular phosphoric acid and sulfuric acid are preferably employed in dilute aqueous form.

If the first reaction step is carried out under superatmospheric pressure, it is recommended to vent the reactor prior to neutralisation with acid. In general, the decarboxylation sets in spontaneously during the addition of the acid, when the suitable pH is reached. If desired, the reaction conditions can be maintained for a certain period of time, which can be a few minutes to several hours, in order to bring the decarboxylation to completion.

The compound I is isolated in a customary manner by work-up of the reaction mixtures of the second reaction step by customary work-up methods, for example by extractive work-up of the liquid reaction mixture with an organic solvent or by removing the solvent and isolating the target compound from the residue obtained. Prior to work-up, it is recommended to neutralize the reaction mixture of the second reaction step with a base to a pH≦6, for example pH 6–7. Suitable bases are alkali metal hydroxides, alkali metal carbonates, alkali metal bicarbonates, alkaline earth metal carbonates and alkaline earth metal hydroxides. Usually, alkali metal hydroxides and in particular aqueous sodium hydroxide solution are used for neutralization.

In the process according to the invention, owing to the resulting salt loading, it is frequently advantageous to remove all or some of the aqueous reaction medium of the $2^{nd}$ reaction step, preferably after neutralization, by distillation or by evaporation under reduced pressure, and to extract the residue with a suitable organic solvent, to isolate the compound I. Here, the person skilled in the art will choose solvents in which the desired product is soluble, but not the salts formed during neutralization. Typical organic solvents for extraction are $C_2$–$C_6$-alcohols, such as ethanol, n-propanol, isopropanol, n-butanol, isobutanol, amyl alcohol and isoamyl alcohol, aromatic hydrocarbons, such as toluene, ethylbenzene and xylenes. The target compound I is then obtained after concentration of the extract to dryness and can be purified further and worked up in a customary manner.

It is also possible to work up the aqueous reaction medium of the $2^{nd}$ reaction step, preferably after neutralization, by extraction with a polar solvent which is not or only sparingly miscible with water, for example by extraction with a $C_4$–$C_6$-alcohol, such as n-butanol, isobutanol, amyl alcohol or isoamyl alcohol, or with one of the abovementioned aromatic hydrocarbons. The extraction can be carried out in portions or continuously.

To illustrate the process according to the invention, a typical process procedure for converting the compounds II into the 2-pyrazolin-5-ones is described below:

The compounds II are dissolved in an aqueous solution of the alkali metal hydroxide. The concentration of the solution is generally in the range from 10 to 50% by weight and is calculated such that 5–12 mol of alkali metal hydroxide are present per mole of the compound II. This solution is heated in an autoclave at a temperature in the range from 150 to 180° C., resulting in a pressure in the range from 5 to 7 bar. The reaction temperature is maintained for 2 to 10 hours. After cooling to room temperature and venting to normal pressure, an amount of mineral acid which is sufficient for adjusting the pH is added. The pH is preferably in the range from 0 to 6 and in particular in the range from 1 to 3. Spontaneous evolution of $CO_2$ occurs. The mixture is then neutralized with a base to pH 6–7. The reaction mixture is then evaporated under reduced pressure to dryness, and the solid residue is extracted, for example in a Soxhlet apparatus, using a suitable solvent. Evaporation of the solvent gives the N-substituted 2-pyrazolin-5-one of the formula I in high yield and purity. Instead of evaporation/extraction, it is also possible to isolate the compound I from the aqueous reaction mixture after neutralization to pH 6–7 by extraction with a suitable solvent, for example isobutanol or toluene.

For further illustration of the invention, examples are given below.

EXAMPLE 1

Preparation of 1-methyl-2-pyrazolin-5-one

In a 250 ml autoclave, 10 g (0.0623 mol) of 5-chloro-1-methyl-4-pyrazolecarboxylic acid were dissolved in 100 g of 25% by weight strength aqueous sodium hydroxide solution (=0.623 mol). The solution was heated at 175° C. for 6 h. During this time, the pressure increased to 6 bar. After cooling, the autoclave was vented to atmospheric pressure. The reaction mixture was then adjusted to pH 1.5 using 60% by weight strength sulfuric acid. This resulted in evolution of $CO_2$. After several minutes, the pH was adjusted to 6.5 using 25% by weight strength aqueous sodium hydroxide solution, and the resulting solution was concentrated under reduced pressure to dryness. The solid residue was transferred into a Soxhlet apparatus and continuously extracted with ethanol. Distillative removal of the ethanol under reduced pressure gave 5.7 g of the target compound of a purity of 98.9% (determined by gas chromatography). The melting point was 113° C. This corresponds to a yield of 92.3% of theory. The product was identified by the mixed melting point with an authentic sample.

EXAMPLE 2

Preparation of 1-ethyl-2-pyrazolin-5-one=5-hydroxy-1-ethylpyrazole 4 g of 5-chloro-1-ethyl-4-pyrazolecarboxylic acid were dissolved in 40 g of 25% by weight strength aqueous sodium hydroxide solution and reacted similarly to the procedure described in Example 1. The reaction temperature of the first reaction step was 170° C., the reaction pressure was 7.5 bar. The duration of the reaction was 8 h. Work-up in the manner described for Example 1 gave 2.3 g of the target compound of a purity of 99.7% (determined by gas chromatography). This corresponds to a yield of 89.4% of theory. The melting point was 88° C. The product was identified by the mixed melting point with an authentic sample.

EXAMPLE 3

Preparation of 1-methyl-2-pyrazolin-5-one, Work-up by Liquid-liquid Extraction

As in Example 1, 10 g of 5-chloro-1-methylpyrazole-4-carboxylic acid were initially reacted with 100 g of 25% by weight strength aqueous sodium hydroxide solution and then under acidic conditions. The acidic reaction mixture was neutralized to pH 6.5 using 25% by weight strength aqueous sodium hydroxide solution and the reaction mixture was then transferred into a liquid-liquid extractor and extracted with isobutanol at the boiling point of the solvent. Isolation of the organic phase and distillative removal of the isobutanol gave 5.8 g of 1-methyl-2-pyrazolinone (purity according to GC: 98.1%). The melting point was 112° C. The yield was 92.5% of theory.

We claim:

1. A process for preparing N-substituted 2-pyrazolin-5-ones of the formula I

(I)

in which

R is $C_1$–$C_8$-alkyl, $C_5$–$C_8$-cycloalkyl, phenyl, naphthyl or phenyl-$C_1$–$C_4$-alkyl which may be unsubstituted or may carry one or more substituents which are inert towards aqueous alkali, which comprises reacting a compound of the formula II

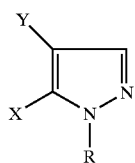
(II)

in which

X is halogen, and

Y is CN or a group R'(O)C, in which R' is a hydroxyl group or a radical which can be hydrolyzed using alkali metal hydroxide, and R has the meanings mentioned for formula I, at elevated temperature with a molar excess of alkali metal hydroxide in an aqueous reaction medium, and then adjusting the pH to pH$\leq$6 by adding an acid.

2. A process as claimed in claim 1, wherein the compound of the formula II is reacted with at least 3 mol of alkali metal hydroxide, based on 1 mol of the compound II.

3. A process as claimed in claim 1, wherein the reaction with aqueous alkali metal hydroxide is carried out at a temperature above 90° C.

4. A process as claimed in claim 1, wherein the acid is added at a temperature in the range from 0 to 100° C.

5. A process as claimed in claim 1, wherein compounds of the formula II are used in which Y is a group R'(O)C;

R' is $C_1$–$C_4$-alkyloxy or OH;

X is chlorine or bromine; and

R has one of the meanings mentioned for formula I.

6. A process as claimed in claim 1, wherein the reaction is carried out in an aqueous 10–50% by weight strength sodium hydroxide solution.

* * * * *